United States Patent [19]

Hughes

[11] 4,117,016

[45] Sep. 26, 1978

[54] PROCESS FOR STRUCTURAL MODIFICATION OF UNSATURATED ALCOHOLS

[75] Inventor: William B. Hughes, Bartlesville, Okla.

[73] Assignee: Phillips Petroleum Company, Bartlesville, Okla.

[21] Appl. No.: 801,447

[22] Filed: May 27, 1977

[51] Int. Cl.$^2$ .................. C07C 45/00; C07C 29/00; C07C 27/00

[52] U.S. Cl. .................. 260/593 R; 260/586 R; 260/590 R; 260/596; 260/598; 260/599; 260/601 R; 260/603 R; 260/603 C; 568/715; 568/822; 568/835; 568/902; 568/903

[58] Field of Search .......... 260/642 A, 586 R, 590 R, 260/593 R, 596, 598, 599, 601 R, 603 HF, 603 R

[56] References Cited

U.S. PATENT DOCUMENTS

| | | | |
|---|---|---|---|
| 3,458,547 | 7/1969 | Coffey | 260/638 B |
| 3,479,403 | 11/1969 | Maclean | 260/596 |
| 3,655,735 | 4/1972 | Pummer et al. | 260/642 A |
| 3,733,362 | 5/1973 | Biale | 260/632 HF |
| 3,755,451 | 8/1973 | Kurtz et al. | 260/642 A |
| 3,778,477 | 12/1973 | Mueller et al. | 260/603 R |
| 3,836,553 | 9/1974 | Fenton | 260/596 |

*Primary Examiner*—Joseph E. Evans

[57] ABSTRACT

Structural modification of olefinically unsaturated alcohols is achieved by contacting the unsaturated alcohol under reaction conditions with a catalytic amount of a catalyst composition comprising a ruthenium hydride complex of tertiary phosphine ligands.

10 Claims, No Drawings

PROCESS FOR STRUCTURAL MODIFICATION OF UNSATURATED ALCOHOLS

This invention relates to the structural modification of unsaturated alcohols.

Structural modification of unsaturated alcohols such as by isomerization to the corresponding aldehydes and ketones is well known. Such reactions have been catalyzed by strong acids such as sulfuric acid, metal oxides such as aluminum and zinc oxides, or copper and metal complexes such as iron pentacarbonyl. Such systems have certain disadvantages. For example, although strong acids isomerize some branched unsaturated alcohols, they simultaneously dehydrate others to diolefins. Similarly, isomerization with metal oxides is accompanied by a number of side reactions. Copper has a relatively low activity and requires high temperature, which leads to dehydrogenation and, hence, formation of unsaturated carbonyl compounds. The metal complexes generally give low yields, particularly in the production of aldehydes. Thus, there is desired in the art a system which can readily provide the structural modification of unsaturated alcohols while avoiding the various disadvantages heretofore experienced in the art.

It is thus an object of this invention to provide an improved process for the structural modification of unsaturated alcohols.

Other aspects, objects and advantages of the present invention will be apparent to those skilled in the art from a study of the following detailed description and the appended claims.

In accordance with this invention, a process is provided for the structural modification of an olefinically unsaturated alcohol which comprises contacting the unsaturated alcohol under reaction conditions with a catalytic amount of a catalyst comprising a ruthenium hydride complex of tertiary phosphine ligands.

The term "structural modification" as employed herein includes not only isomerization of olefinically unsaturated alcohols to saturated aldehydes or ketones and/or to isomeric olefinically unsaturated alcohols, but also the disproportionation of unsaturated olefinic alcohols whereby the olefinically unsaturated alcohol is converted to the corresponding saturated alcohol and unsaturated aldehyde or ketone.

The catalyst composition employed in the process of this invention comprises a ruthenium hydride complex of the formula $$(R_3P)_3RuHXY_m$$

wherein each R is independently selected from hydrocarbyl radicals containing from 1 to 10 carbon atoms, such as, for example, alkyl, cycloalkyl and aryl, and combinations thereof, such as aralkyl, alkaryl, arylcycloalkyl, and the like; X is selected from the group consisting of hydrogen, chlorine, bromine and iodine; Y is CO or $PR_3$; and $m$ is 0 or 1. Examples of ruthenium compounds include:

dihydridotetrakis(triphenylphosphine)ruthenium(II),
hydridochlorotris(triphenylphosphine)ruthenium(II),
hydridochlorocarbonyltris(trihenylphosphine)ruthenium(II),
hydridobromocarbonyltris(triphenylphosphine)ruthenium(II),
hydridoiodocarbonyltris(triphenylphosphine)ruthenium(II),
hydridochlorocarbonyltris(trihexylphosphine)ruthenium(II),
hydridochlorocarbonyltris(tribenzylphosphine)ruthenium(II),
hydridochlorocarbonyltris(tricyclohexylphosphine)ruthenium(II),
hydridochlorocarbonyltris(tri-[4-butylphenyl]phosphine)ruthenium(II),
hydridochlorocarbonyltris(diethylphenylphosphine)ruthenium(II)

and admixtures thereof.

In a presently preferred embodiment of this invention the catalyst composition consists essentially of the above-described ruthenium hydride complex compound.

The ruthenium complexes of this invention can be prepared by any convenient method known in the art. Generally convenient methods are disclosed in Inorganic Synthesis, Volume XIII, pages 131-134 (1972) and Volume XV, pages 45-65 (1974) and the Journal of the Chemical Society (A), 1970, 2947-2954. An example of a convenient method is the reaction of a suitable ruthenium compound with a trihydrocarbyl phosphine compound and formaldehyde, such as the reaction of ruthenium trichloride, triphenylphosphine and formaldehyde in 2-methoxy-ethanol to form hydridochlorocarbonyltris(triphenylphosphine)ruthenium(II).

The ruthenium complexes employed in this invention are air-sensitive and are generally unstable in the presence of air or oxygen-containing atmospheres. Accordingly, the preparation and uses of these complexes should exclude or appreciably restrict air or oxygen, as well as exclude any reactive substance or atmosphere which may tend to reduce the effectiveness of the complex in a conversion process.

While not essential to the practice of this invention, the ruthenium hydride complex can be anchored to a polymeric substrate through the organophosphine ligand of the complex. Such procedures are known in the art, and certain of the phosphine ligand polymeric anchor materials are commercially available, such as polymer-bound triphenylphosphine on styrene/divinyl benzene copolymers of varying degrees of crosslinking. The use of such polymer-anchored catalysts enables the practice of typical heterogeneous catalysis techniques such as, for example, a continuous process or ease of catalyst recovery.

The olefinically unsaturated alcohols which are employed in the process of the present invention can be represented by the formula

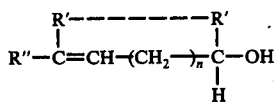

wherein each R' and R" is separately selected from the group consisting of hydrogen and hydrocarbyl radical groups having from 1 to 8 carbon atoms, and $n$ has a value ranging from 0 to 17; and wherein the two R' groups can together represent an alkylene radical having from 1 to 16 carbon atoms. The total number of carbon atoms in the unsaturated alcohol is in the range of 4 to 20. Each hydrocarbyl radical group can be alkyl, cycloalkyl or aryl, or a combination thereof such as alkaryl, aralkyl or the like. In a presently preferred embodiment, n has a value in the range of 0 to 4 and each R' and R" is hydrogen or a lower alkyl of 1 to 4 carbon atoms.

Examples of olefinically unsaturated alcohols which can be employed in the process of this invention include 3-buten-2-ol, 3-buten-1-ol, 3-penten-2-ol, 2-methyl-7-butyl-4-tridecen-6-ol, 11-eicosen-10-ol, 1-cyclohexyl-5-cyclopentyl-3-penten-1-ol, 1-phenyl-4-p-tolyl-3-buten-2-ol, 2-methyl-4-hexen-2-ol, 4-hexen-1-ol, 3-cyclohexen-1-ol, and the like.

The amount of the ruthenium complex employed in the process of this invention can vary widely. The amount of the complex employed is at least a catalytic amount, i.e., an amount of the complex which promotes the conversion of at least a portion of the unsaturated alcohol. In general, the amount of complex is in the range of from about 0.001 to about 1 mole of the ruthenium complex per mole of the olefinic alcohol, preferably about 0.002 to about 0.1 mole of the ruthenium complex per mole of reactant. When the above-described polymer-anchored ruthenium complex is utilized, these ranges are expressed in terms of gram atoms of ruthenium per mole of reactant.

The process of this invention can be carried out either as a batch or as a continuous process using any conventional apparatus.

The process of this invention is generally carried out in the absence of an added reaction diluent, although such diluents can be used if desired, provided that the diluent be inert to the reaction. Typical diluents that can be used are aromatic hydrocarbons, such as benzene and toluene, and chlorinated hydrocarbons, such as chlorobenzene and chloroform. The amount of diluent, if used, is not critical and can range from 1 to 0.02 part of diluent per part of reactant, by volume.

The process of the present invention is preferably carried out in the absence of added hydrogen.

The process of this invention can be carried out at a temperature in the approximate range of about 0° to about 200° C., preferably about 25° to about 150° C.

The pressure utilized for the process of this invention is not critical, but is desirably sufficient to maintain the reactant and products substantially in the liquid phase at the temperature employed. If desired, the operating pressure can be supplied by the use of an inert gas, such as nitrogen, helium or argon.

Depending on the mode of reaction and other factors such as operating temperature, catalyst activity and reactivity of the starting material, the complex:alcohol contact time can vary from 1 minute to about 48 hours or more. The particular time employed for the conversion reaction can often be readily determined by measuring the rate at which the reaction mixture approaches the equilibrium composition for the mixture.

The reaction product or products of this invention can be separated from the reaction mixture by any method known in the art. Suitable separation techniques include filtration, fractional distillation, fractional crystallization, macroscale chromatography techniques, and the like.

The process of the invention is useful for converting less valuable compounds to compounds having greater value.

The following examples illustrate the invention:

EXAMPLE I 2.54 Grams (32 mmole) of 2-buten-1-ol (purity 90.6%) and 0.1 gram (0.105 mmole) of previously prepared hydridochlorocarbonyltris(triphenylphosphine)-ruthenium(II) were charged to a Diels-Alder tube, under nitrogen. The mixture was heated, with stirring, to 60°–64° C. for a total of 10 hours, with an overnight period at room temperature without stirring during the run. The reaction mixture was then cooled to room temperature and analyzed by gas-liquid chromatography (glc). The structures of the products were determined by comparison of glc retention times with those of known compounds, and by glc-mass spectrographic analysis of a distilled sample of the crude reaction mixture.

The results obtained are as follows:
Reaction mixture, weight percent of mixture (by glc):

butyraldehyde, 14.1;
1-butanol, 11.6;
crotonaldehyde, 8.8;
3-buten-1-ol, 6.6; and
2-buten-1-ol, 53.8 (starting material).

EXAMPLE II

The procedure of Example I was followed except that the reaction temperature was 60°–72° C. while employing 2.51 grams (33.6 mmole) of 3-buten-1-ol (purity 96.3%) and 0.1 gram (0.105 mmole) of the same catalyst.

The results are as follows:
Reaction mixture, weight percent of mixture (by glc):

butyraldehyde, 16.3;
1-butanol, 10.9;
crotonaldehyde, 7.5*;
2-buten-1-ol, 41.7; and
3-buten-1-ol, 18.4 (starting material).

* position of double bond not established

EXAMPLE III

The procedure of Example II was followed except that the reaction temperature was increased to 85°–95° C. and the reaction time was increased to about 48 hours, while employing 2.51 grams (33.6 mmole) of 3-buten-1-ol (purity 96.3%) and 0.1 gram (0.105 mmole) of the same catalyst.

The results are as follows:
Reaction mixture, weight percent of mixture (by glc):

butyraldehyde, 14.4;
1-butanol, 15.9;
crotonaldehyde, 7.0*;
2-buten-1-ol, 44.6; and
3-buten-1-ol, 12.3 (starting material).

* position of double bond not established

EXAMPLE IV

The procedure of Example I was followed while employing 3.05 grams (25.6 mmole) of 3-methyl-2-buten-1-ol (purity 72.3%) and 0.1 gram (0.105 mmole) of the same catalyst.

The reaction mixture contained the following compounds: isovaleraldehyde, isoamyl alcohol, 3-methyl-2-butenal, and 3-methyl-3-buten-1-ol. A quantitative determination of these products was not made.

EXAMPLE V

The procedure of Example I was followed except that the reaction temperature was increased to 130° C. for 10 hours, while employing 2.54 grams (21.4 mmole) of 3-methyl-2-buten-1-ol (purity 72.3%) and 0.1 gram (0.105 mmole) of the same catalyst. The same products were obtained as in Example IV. A quantitative determination was not made.

EXAMPLE VI

The procedure of Example I was followed except that the reaction was carried out at 60° C. for 8 hours, while employing 2.5 grams (31.1 mmole) of 3-buten-2-ol (purity 89.7%) and 0.1 gram (0.105 mmole) of the same catalyst.

The results are as follows:
Reaction mixture, weight percent of mixture (by glc):

methylethyl ketone, 19.7;
methylvinyl ketone, 2.0;
2-butanol, 3.6; and
3-buten-2-ol, 71.8 (starting material).

EXAMPLE VII

The procedure of Example I was followed while employing 1.02 grams (11.5 mmole) of 3-methyl-3-buten-1-ol (purity 96.6%) and 0.1 gram (0.105 mmole) of the same catalyst.

The results are as follows:
Reaction mixture, weight percent of mixture (by glc):

3-methyl-2-buten-1-ol, 1.3; and
3-methyl-3-buten-1-ol, 91.8 (starting material).

EXAMPLE VIII

The procedure of Example I was followed except that no catalyst was present in the reaction system, while employing 1.26 grams (16.8 mmole) of 3-buten-1-ol (purity 96.3%). No reaction occurred.

EXAMPLE IX

The procedure of Example I was followed except that the reaction temperature was 60°–72° C. and that 0.1 gram of dichlorodicarbonylbis(triphenylphosphine)-ruthenium(II) was used in place of the ruthenium complexes of this invention, employing 2.54 grams (32 mmole) of 2-buten-1-ol (purity 90.6%). No reaction occurred.

The above Examples I–VI demonstrate the operability of the instant invention for the conversion of unsaturated alcohols to aldehydes or ketones and, in some cases, another olefinic alcohol. Additionally, the corresponding saturated alcohol and an unsaturated aldehyde are formed by disproportionation. Example VII shows that olefins outside the scope of this invention do not undergo conversion to the desired carbonyl compounds. Example VIII shows that no isomerization occurs in the absence of a catalyst. Example IX shows that a ruthenium complex outside the scope of this invention does not promote conversion of an olefinically unsaturated alcohol.

Reasonable, variations and modifications, which will be apparent to those skilled in the art, can be made in this invention without departing from the spirit and scope thereof.

What is claimed is:

1. A process for the production of a carbonyl compound from an olefinically unsaturated alcohol having from 4 to 20 carbon atoms per molecule and which is represented by the formula $$R''-C=CH-(CH_2)_n-\underset{H}{\overset{R'}{\underset{|}{C}}}-OH$$

wherein R' and R'' are independently selected from the group consisting of hydrogen and a hydrocarbyl radical having from 1 to 8 carbon atoms, n is an integer having a value in the range of 0 to 17, wherein the two R' groups can together represent an alkylene radical having from 1 to 16 carbon atoms, which comprises contacting said olefinically unsaturated alcohol under reaction conditions with a catalytic amount of a catalyst composition comprising a ruthenium II hydride complex of a tertiary phosphine ligand which is represented by the formula $$(R_3P)_3RuHXY_m$$

wherein each R is a hydrocarbon radical having from 1 to 10 carbon atoms, X is hydrogen or a halogen selected from the group consisting of chlorine, bromine and iodine, Y is selected from the group consisting of CO and $PR_3$, and m is an integer having a value of 0 or 1.

2. A process according to claim 1 wherein said contacting is carried out at a temperature in the approximate range of 0° to 200° C.

3. A process according to claim 1 wherein said contacting is carried out at a pressure sufficient to maintain the reactants substantially in the liquid phase.

4. A process according to claim 1 wherein said ruthenium hydride complex is employed in an amount in the range of from about 0.001 to 1 mole of said ruthenium hydride complex per mole of said olefinically unsaturated alcohol.

5. A process according to claim 1 wherein said contacting is carried out for a time in the range of from 1 minute to 48 hours.

6. A process according to claim 1 wherein said olefinically unsaturated alcohol is 2-buten-1-ol.

7. A process according to claim 1 wherein said olefinically unsaturated alcohol is 3-buten-2-ol.

8. A process according to claim 1 wherein said olefinically unsaturated alcohol is 3-buten-1-ol.

9. A process according to claim 1 wherein said olefinically unsaturated alcohol is 3-methyl-2-buten-1-ol.

10. A process according to claim 1 wherein said ruthenium II hydride complex is hydridochlorocarbonyltris(triphenylphosphine)ruthenium(II).

* * * * *